(12) United States Patent
Bills

(10) Patent No.: US 6,712,608 B2
(45) Date of Patent: Mar. 30, 2004

(54) ANATOMICALLY CONTOURED MATRIX BANDS FOR USE IN DENTAL RESTORATION PROCEDURES

(75) Inventor: Dan J. Bills, Salt Lake City, UT (US)

(73) Assignee: Ultradent Products, Inc., South Jordan, UT (US)

( * ) Notice: Subject to any disclaimer, the term of this patent is extended or adjusted under 35 U.S.C. 154(b) by 159 days.

(21) Appl. No.: 09/838,694

(22) Filed: Apr. 19, 2001

(65) Prior Publication Data

US 2002/0172920 A1 Nov. 21, 2002

(51) Int. Cl.[7] .................................................. A61C 5/04
(52) U.S. Cl. .......................................................... 433/39
(58) Field of Search .............................. 433/39, 40, 41

(56) References Cited

U.S. PATENT DOCUMENTS

| | | | | |
|---|---|---|---|---|
| 2,611,182 A | * | 9/1952 | Tofflemire | 433/39 |
| 3,145,472 A | * | 8/1964 | Tofflemire | 433/39 |
| 3,421,222 A | * | 1/1969 | Newman | 433/39 X |
| 3,842,505 A | * | 10/1974 | Eanes | 433/39 |
| 4,704,087 A | * | 11/1987 | Dragan | 433/39 |
| 4,824,365 A | * | 4/1989 | von Weissenfluh | 433/39 X |
| 5,607,302 A | | 3/1997 | Garrison et al. | 433/39 |
| 5,730,592 A | * | 3/1998 | Meyer | 433/39 |
| 6,325,625 B1 | | 12/2001 | Meyer | |

* cited by examiner

Primary Examiner—Nicholas D. Lucchesi
(74) Attorney, Agent, or Firm—Workman, Nydegger

(57) ABSTRACT

The invention comprises an asymmetrically shaped matrix band. The asymmetrical shape of the matrix band provides form for molding a dental filling into a shape that closely approximates the asymmetrical and generally trapezoidal shape of a tooth. The matrix band comprises a cross-sectional area that curves asymmetrically in the vertical direction along a curve that is constrained by two radii. The first radius is applied near the top of the matrix band and has a magnitude that is approximately one third of the magnitude of the second radius that is applied at the bottom of the matrix band. The curvature of the cross-sectional area enables the matrix band to also provide form for molding a dental filling with a contact point in the anatomically correct location on a restored tooth.

21 Claims, 4 Drawing Sheets

ANATOMICALLY CONTOURED MATRIX BANDS FOR USE IN DENTAL RESTORATION PROCEDURES

BACKGROUND OF THE INVENTION

1. The Field of the Invention

The present invention relates to the field of matrix bands for use in dental procedures. More particularly, the present invention relates to anatomically contoured matrix bands for providing form for molding a dental filling into a shape that more closely approximates the anatomical shape of a tooth.

2. The Prior State of the Art

The filling of cavities is one of the most common dental procedures. In order to treat cavities the dental practitioner removes the infected portion of the tooth so as to form a hollow and then deposits a filling material, such as a composite, a resinous material, or an amalgam, into the tooth hollow.

During the dental filling procedure, a matrix band is typically wrapped around the side of the tooth to approximately define the desired shape of the finished tooth and to keep the filling material from flowing beyond the desired tooth boundary. A matrix band typically comprises a thin metallic or plastic strip that is flexible and can be bent around the tooth being restored. The matrix band is particularly useful because it provides form for the desired shape of the resultant filling. However, if the matrix band is not properly held in place then too much or too little filling material may be deposited into the tooth preparation, thereby distorting the configuration of the restored tooth.

An improper filling can lead to dental discomfort, misaligned teeth, capture of food particles, infections, and other dental problems. To avoid these problems, and to fix a distorted dental filling, it may be necessary to grind or drill the filling material down to the proper shape. However, it is desirable to avoid this process because it increases the time and cost of performing the filling procedure and can create anxiety and discomfort for the patient. Accordingly, it is desirable to place the matrix band against the tooth in such a way as to approximate the desired shape of the restored tooth so as to minimize the amount of post-filling shaping of the tooth restoration.

One problem with existing matrix bands, however, is that they do not naturally assume and conform to the anatomical shape of the tooth. In other words, they only grossly approximate the asymmetric contours of a tooth. Moreover, while flexible and deformable, non-anatomically configured matrix bands do not readily conform to the anatomically correct shape of the tooth being treated, particularly where a hollow exists.

Once the matrix band is placed into the desired placement, it is typically held in place with small dental wedges and/or one or more matrix band retainers. Even though such external devices provide some retention and conformation of the matrix band, non-anatomical matrix bands have the tendency to deform and/or slip out of the desired position.

If the matrix band slips out of its proper orientation during the filling procedure, the dental restoration can be distorted, thereby requiring additional shaping and potentially causing additional discomfort to the patient. It may also be dangerous for the matrix band to slip out of position during the filling procedure. For example, the matrix band can potentially get aspirated, lodged the patient's throat, or scrape against sensitive mouth tissue, causing additional discomfort to the patient.

When restoring a tooth, it is important to form the contact point between the restored tooth and the adjacent tooth (or teeth) at the anatomically correct location, which is approximately two thirds of the way up from the gingiva to the top of the tooth. If the contact point is placed to low or too high then the tooth and adjacent teeth can become misaligned. This can also lead to other problems such as discomfort, capture of food particles, infections, and the like. Accordingly, it is desirable to provide a form that molds the contact point of the restored tooth at the anatomically correct location.

One problem with existing matrix bands, however, is that they often form the contact point too low. The reason for this is that they are symmetrically curved and consequently mold the dental filling with the contact point centrally disposed between the top and bottom edges of the matrix band and tooth, failing to accommodate for the generally trapezoidal shape of the tooth.

Accordingly, there is currently a need in the art for an improved matrix band that conforms to the asymmetrical and generally trapezoidal shape of teeth.

SUMMARY OF THE INVENTION

The present invention is directed to anatomically contoured matrix bands for providing an appropriate form for molding dental fillings into a shape that closely approximates the desired shape of the restored tooth and for molding the resultant filling with a contact point that is located in the anatomically correct location.

The matrix band of the invention comprises a thin strip of metal or plastic comprising two curves, a longitudinal curve that is substantially symmetrical (i.e., has a single radius of curvature) and a latitudinal curve that has at least two different radii of curvature. The longitudinal curve symmetrically extends from a first end of the matrix band to an opposite end of the matrix band. The latitudinal curve asymmetrically extends from a top edge of the matrix band to a bottom edge of the matrix band.

In a preferred embodiment, the shape of the latitudinal curve is defined by a first radius of curvature and a second radius of curvature. The first radius of curvature applies generally to the upper ⅓ of the matrix band and the second radius of curvature applies generally to the lower ⅔ of the matrix band. The magnitude of the first radius of curvature is significantly less than that of the second radius. In a preferred embodiment, the first radius is approximately one third the magnitude of the second radius.

In another embodiment, a flange extends from the bottom edge of the matrix band and has a third radius of curvature. The third radius preferably curves in a direction opposite to the direction of the first and second radius. The magnitude of the third radius of curvature is preferably approximately twice the magnitude of the first radius.

The different curvatures of the matrix band proportionately approximate the anatomical shape of one or more typically-sized teeth such that when the matrix band is disposed about an appropriate tooth receiving a dental filing, the matrix band is able to substantially conform to the asymmetrical, and generally trapezoidal, shape of the original tooth in both the horizontal and vertical directions.

One benefit of the invention is that it generally minimizes the amount of shaping that is required to complete the restoration of a tooth because it is able to mold the dental filling of the restored tooth into a shape that closely approximates the correct anatomy of the original tooth. The matrix band also molds the dental filling so as to have a contact point with one or both adjacent teeth in the anatomically correct location on the restored tooth. Additionally, because the matrix band of the invention conforms to the asymmetrical contours of a tooth, it is easily placed and held in proper placement against the tooth during dental filling procedures.

These and other features and advantages of the present invention will become more fully apparent from the following description and appended claims, or may be learned by practicing the invention as set forth below.

BRIEF DESCRIPTION OF THE DRAWINGS

A more extensive description of the present invention, including the above-recited features and advantages, will be rendered with reference to the specific embodiments that are illustrated in the appended drawings. Because these drawings depict only exemplary embodiments, the drawings should not be construed as imposing any limitation on the present invention's scope. As such, the present invention will be described and explained with additional specificity and detail through use of the accompanying drawings in which.

DETAILED DESCRIPTION OF THE PREFERRED EMBODIMENTS

The present invention relates to an improved matrix band for use in dental restoration procedures. More particularly, the present invention relates to anatomically contoured matrix bands which provide form for molding dental fillings so as to approximate the actual shape of a tooth. Such matrix bands are much better able to conform to the correct anatomical shape of a tooth compared to matrix bands having a more regular curvature.

Figure 1:
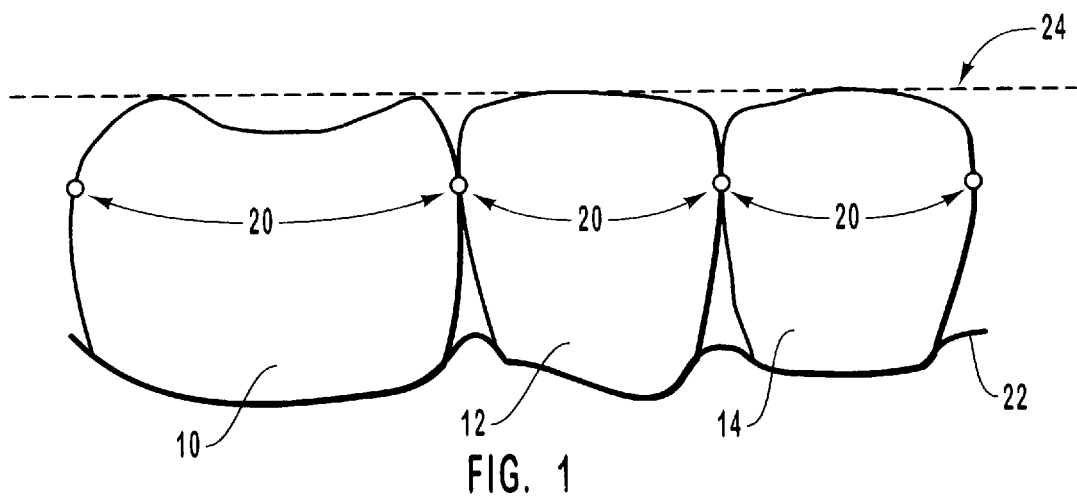
FIG. 1 is a side view of three teeth comprising a molar and two bicuspids.

FIG. 1 is provided to illustrate the general shape of teeth that are commonly treated with dental filling procedures that involve the use of a matrix band. As shown, molar 10 and bicuspids 12 and 14 each comprise a generally trapezoidal shape, with the widest dimension located near the top of each tooth and the narrowest dimension located at the base of each tooth.

Due to their size and shape, molars and bicuspids can advantageously be repaired using matrix bands to approximate the shape of the teeth. Nevertheless, it should be appreciated, however, that use of the matrix bands to repair other types of teeth is also within the scope of the invention. By way of illustration and brevity, molar 10 and bicuspids 12 and 14 will be generically referred to herein as teeth 10, 12, and 14, respectively.

Each of teeth 10, 12, and 14 comprises contact points 20 that are horizontally located where each tooth is the widest and is most likely to make contact with an adjacent tooth. As shown, contact points 20 are located approximately two thirds of the way up from the gingival margin 22 to the occlusal plane 24. The gingival margin 22 is where the teeth 10, 12, and 14 intersect the gingiva. The occlusal plane 24 is the plane extending over and defined by the top surfaces of the teeth 10, 12, and 14.

To avoid problems associated with improperly formed dental restorations it is important to form the contact point of the restored tooth at the anatomically correct position, which is approximately two thirds of the way up from the gingival margin 22 to the occlusal plane 24. If the contact point is placed to low or too high then the restored tooth and adjacent teeth can become misaligned. This can also lead to other problems such as discomfort, capture of food particles, infections, and the like. Accordingly, the anatomically contoured matrix bands of the present invention are beneficial for at least providing means for forming the contact point of a dental restoration at the anatomically correct location, as described herein.

Figure 2:
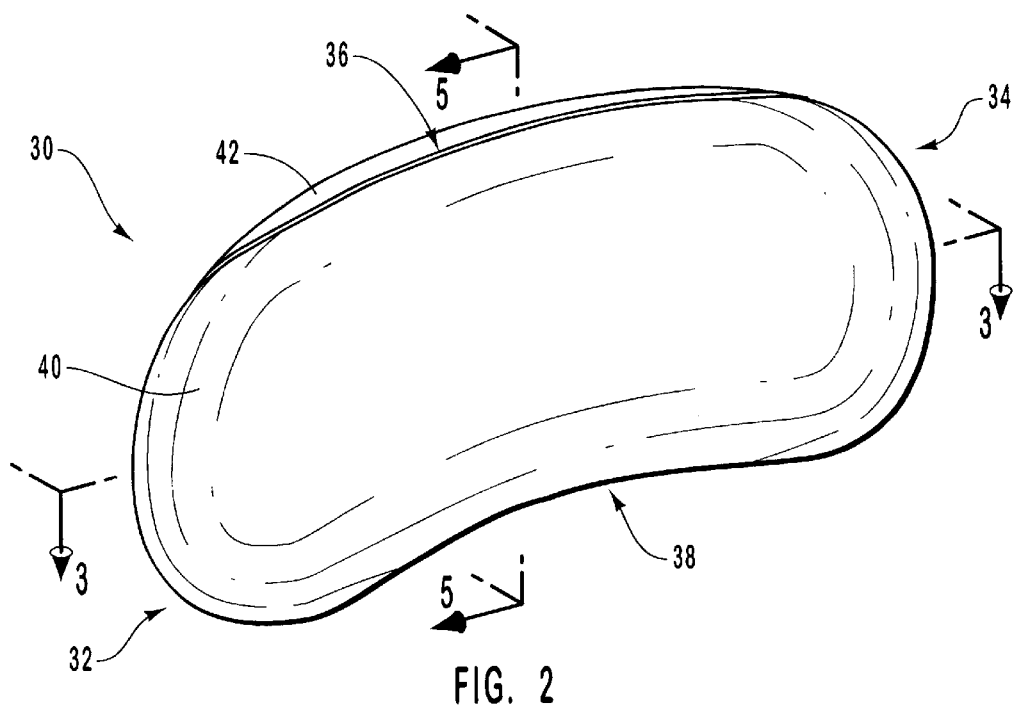
FIG. 2 is a top perspective view of one embodiment of the matrix band of the invention that includes a top edge opposite a bottom edge in a latitudinal dimension, a first end opposite a second end in a longitudinal dimension, and an interior surface opposite an exterior surface.

Turning now to FIG. 2, a presently preferred embodiment of the asymmetrically shaped matrix band of the invention is shown. As shown, matrix band 30 comprises a thin strip that is curved in both the horizontal (or longitudinal) and vertical (or latitudinal) directions. Matrix band 30 includes a body that extends from a first end 32 to a second end 34, from a top edge 36 to a bottom edge 38, and from an interior surface 40 to an exterior surface 42.

Matrix band 30 may advantageously comprise stainless spring steel or any other appropriate metallic, plastic or other flexible and resilient material. Stainless spring steel provides the matrix band 30 with flexibility so that it can be bent around a tooth into a desired position.

FIG. 2 also shows interior surface 40 and exterior surface 42 as being smooth. This, however, should not be construed as a limitation that restricts the scope of the invention. For example, in other embodiments exterior surface 42 may be textured to provide a frictionally-engaging surface against which dental wedges and matrix band retainers can be held in place. Dental wedges and matrix band retainers are commonly used to hold matrix bands in place, but they are susceptible to slipping out of their holding positions. Accordingly, by providing an exterior surface that resists slipping, the dental wedges and matrix band retainers are more likely to remain in place.

Figure 3:
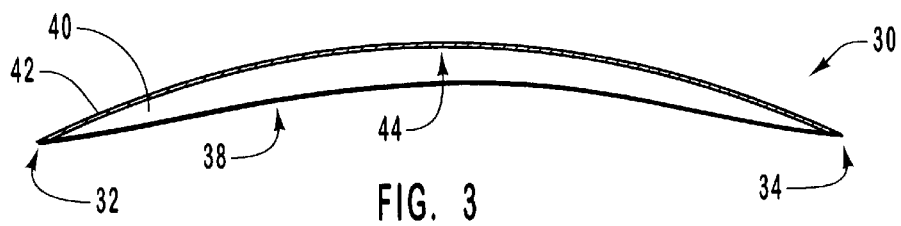
FIG. 3 is a longitudinal cross-sectional view of the matrix band of FIG. 2 taken along line 3—3 illustrating the generally regular longitudinal curvature of the matrix band.

FIG. 3 is a longitudinal cross-sectional view of matrix band 30 of FIG. 2 depicting a generally symmetrical longitudinal curve 44. Longitudinal curve 44 is generally symmetric because it is essentially defined by a single radius of curvature. In a presently preferred embodiment, longitudinal curve 44 has a single internal radius having a magnitude of approximately ⅝ inch.

In a preferred embodiment, the cross-sectional thickness of matrix band 30, defined as the distance between interior surfaces 40 and exterior surface 42, is approximately 0.0015 inch. However, it should be appreciated that the thickness of matrix band 30 and the radius of curvature of longitudinal curve 44 can vary to accommodate various sizes of teeth and for providing a suitable form for a variety of dental filling procedures.

Figure 4:
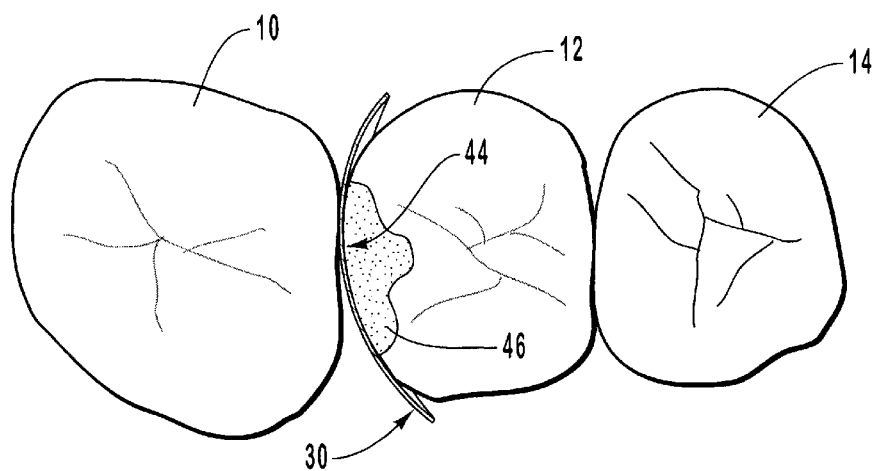
FIG. 4 is a top view of the teeth of FIG. 1 that shows the longitudinal cross-sectional area of the matrix band of FIG. 3 disposed against a tooth having a hollow formed therein.

The symmetric nature of longitudinal curve 44 enables matrix band 30 to be placed in a conformingly correct orientation against the outer circumference of a tooth, as is shown in FIG. 4, which is approximately round in the relevant area of the hollow 46. It should be appreciated, however, that the longitudinal curvature can be irregular or asymmetric as needed for a given procedure.

FIG. 4 is a top view of teeth 10, 12, and 14 of FIG. 1 with tooth 12 comprising a newly formed hollow 46. The hollow 46 is a void in tooth 12 that is made by removing portions of tooth 12 with a drill, burr, or other appropriate device. Typically, a hollow is formed in a tooth to remove carious portions of the tooth that have been damaged by bacterial infection. Once a hollow has been created, dental filling material such as a composite or amalgam can be placed into the dental preparation to restore the tooth to approximately its original size and shape. In order to keep the filling material within the hollow and to control the shape of the resultant filling, a matrix band 30 is at least partially wrapped around the tooth 12 during the filling procedure.

As shown in FIG. 4, longitudinal curve 44 enables matrix band 30 to at least partially wrap around the tooth 12 while in a relaxed condition. This also enables matrix band 30 to provide a form for filling dental preparation 46 with an appropriate filling material.

It should be appreciated that although the first and second ends 32 and 34 of matrix band 30 are not depicted as lying flat against the surface of tooth 12, they can be forced against the tooth surface with any suitable means, such as dental wedges and/or a matrix band retainer. It might be desirable to force ends 32 and 34 against the surface of tooth 12 to help hold matrix band 30 in proper placement and to keep the filling material from flowing beyond the hollow 46.

It should be appreciated that the resultant shape of the dental filling will largely be determined by the form that is provided by matrix band 30. Accordingly, because matrix band 30 comprises a generally symmetrically shaped longitudinal curve 44, the dental filling will also comprise a symmetrically shaped curve around the circumference. This is acceptable because tooth 12 is approximately round. It is not appropriate, however, for the dental filling to be symmetrically shaped in the latitudinal direction because tooth 12 has an asymmetric and generally trapezoidal profile, as shown in FIG. 1, which does not approximate a symmetric curve. This concept will be shown and explained in more detail in reference to FIGS. 5 and 6.

Figure 5:
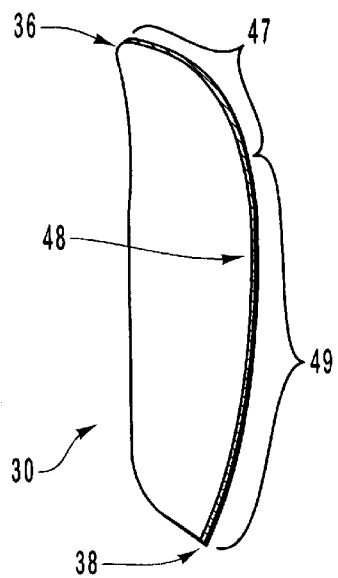
FIG. 5 is a latitudinal cross-sectional view of the matrix band of FIG. 2 taken along line 5—5 illustrating the generally asymmetrical curvature in the latitudinal direction.

FIG. 5 is a cross-sectional view of matrix band 30 of FIG. 2. taken along cutting line 5—5, depicting an irregular, or asymmetric latitudinal curve 48. Latitudinal curve 48 is considered asymmetric because it is controlled or defined by multiple radii. In particular, latitudinal curve 48, as it exists at cutting line 5—5 approximately midway between first end 32 and second end 34, curves more sharply near top edge 36 than at bottom edge 38. As shown in FIG. 2, the asymmetric latitudinal curve 48 spans a majority of the length between first end 32 and second end 34 of the matrix band 30.

In a preferred embodiment, an upper latitudinal curvature 47 having a first radius extends downward from top edge 36 to approximately one third of the total distance between top edge 36 and bottom edge 38. A lower latitudinal curvature 49 having a second radius larger than the first radius extends over the remaining latitudinal distance of latitudinal curve 48 to bottom edge 38. In a preferred embodiment, the first radius has a magnitude that is approximately one third the magnitude of the second radius. For example, the first radius may advantageously have a magnitude of approximately ⅛ inch and the second radius may advantageously have a magnitude of approximately ⅜ inch.

It should be appreciated, however, that the first radius and the second radius can have various magnitudes to enable matrix band 30 to accommodate variously sized teeth, as teeth may vary from person to person and within a given person's own set of teeth. Likewise, the proportional relationship between the first and the second radius can also vary to enable matrix band 30 to accommodate the various contours of different types of teeth.

The asymmetry of latitudinal curve 48 is particularly useful for enabling matrix band 30 to conformingly rest against the generally trapezoidal shape of a tooth in the vertical direction when providing form for filling a dental preparation. This feature of the invention is generally illustrated in FIG. 6.

Figure 6:
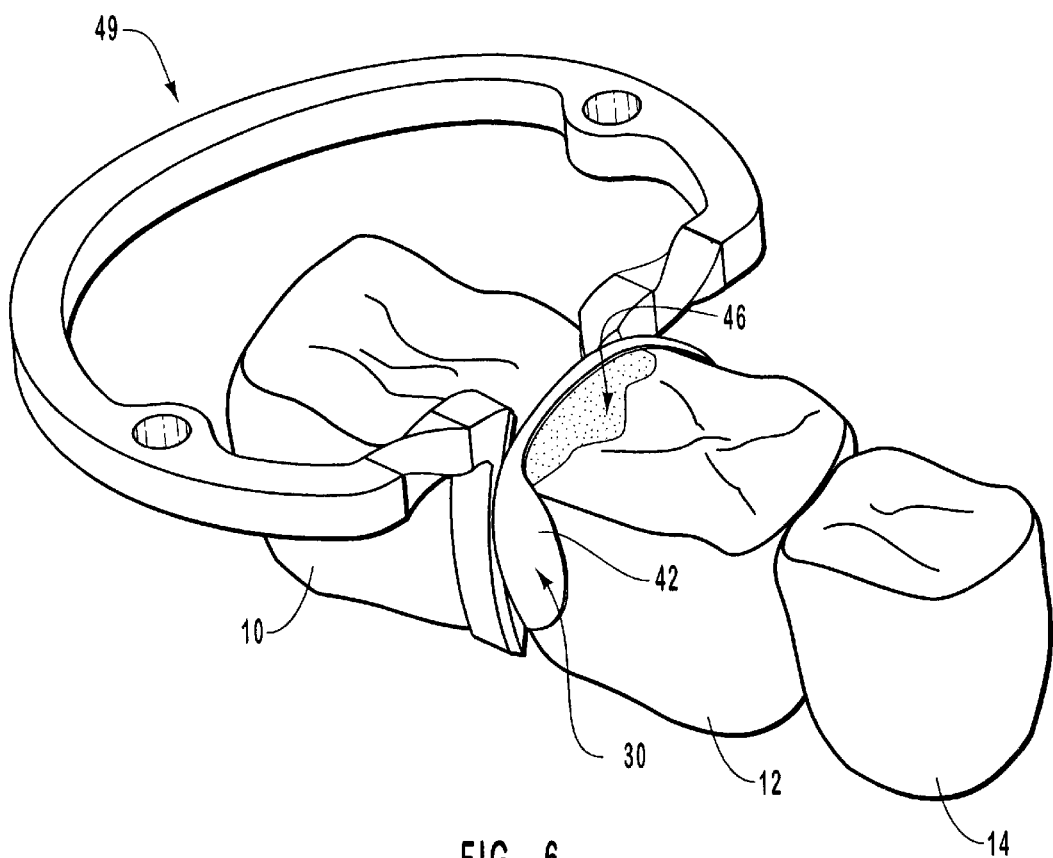
FIG. 6 is a perspective view of a matrix band of the invention placed around a tooth having a hollow dental preparation that is suited for being filled with a filling material, wherein the matrix band is held in place by a matrix band retainer.

FIG. 6 is a top perspective view of teeth 10, 12, and 14 of FIG. 4 with matrix band 30 disposed between teeth 10 and 12. As shown, matrix band 30 conformingly rests against tooth 12, with matrix band retainer 49 disposed against tooth 10 and against outside surface 42 of matrix band 30, thereby holding matrix band 30 in place. Anatomically shaped matrix band retainers that conform to the shape of teeth and which are particularly suitable for use in retaining matrix bands according to the invention are set forth in co-pending U.S. application Ser. No. 09/868,681, filed Apr. 19, 2001 and entitled "Anatomically Shaped Sectional Matrix Band Retainers" now abandoned. For purposes of disclosure, the foregoing application is incorporated herein by reference.

The shape of matrix band 30 is defined by the generally symmetric longitudinal curve 44 described above in relation to FIG. 3 and the asymmetric latitudinal curve described above in relation to FIG. 5. It will readily be appreciated that these curves enable matrix band 30 to conform to the asymmetric and generally trapezoidal shape of tooth 12, as shown in FIG. 6.

It should also be appreciated that the asymmetric curvature of longitudinal curve 48, of the embodiment depicted in FIG. 5, enables matrix band 30 to provide an appropriate form for filling dental preparation 46 so that the resultant filling will closely approximate the desired shape of the restored tooth and will have a contact point located in an anatomically correct location. In other words, the widest portion of the resultant filling will be located approximately two thirds of the way up from the bottom of tooth 12, conforming to the general shape of asymmetric latitudinal curve 48.

It should be appreciated that this is an advantage over symmetrically curved prior art matrix bands. In particular, prior art matrix bands that are symmetrically curved in the longitudinal and latitudinal directions tend to form the contact point near the center of the tooth, which is too low. When the contact point between teeth is formed too low then dental problems can occur, such as misaligned teeth, dental discomfort, capture of food particles, and the like. Accordingly, matrix band 30 is advantageous over the prior art for at least helping to minimize these problems by forming contact points in the anatomically correct location.

Another benefit of the matrix band 30 is that it can minimize the amount of post-treatment shaping that may be required after filling a hollow with a filling material. For example, matrix band 30 is able to provide a form for molding the resultant filling into a shape that more closely approximates the original shape of the tooth to be restored so that only minimal shaping, if any, is required to complete the restoration procedure. This is beneficial for at least minimizing the time and cost associated with performing the procedure, and it also reduces potential anxiety and discomfort suffered by the patient.

Figure 7:
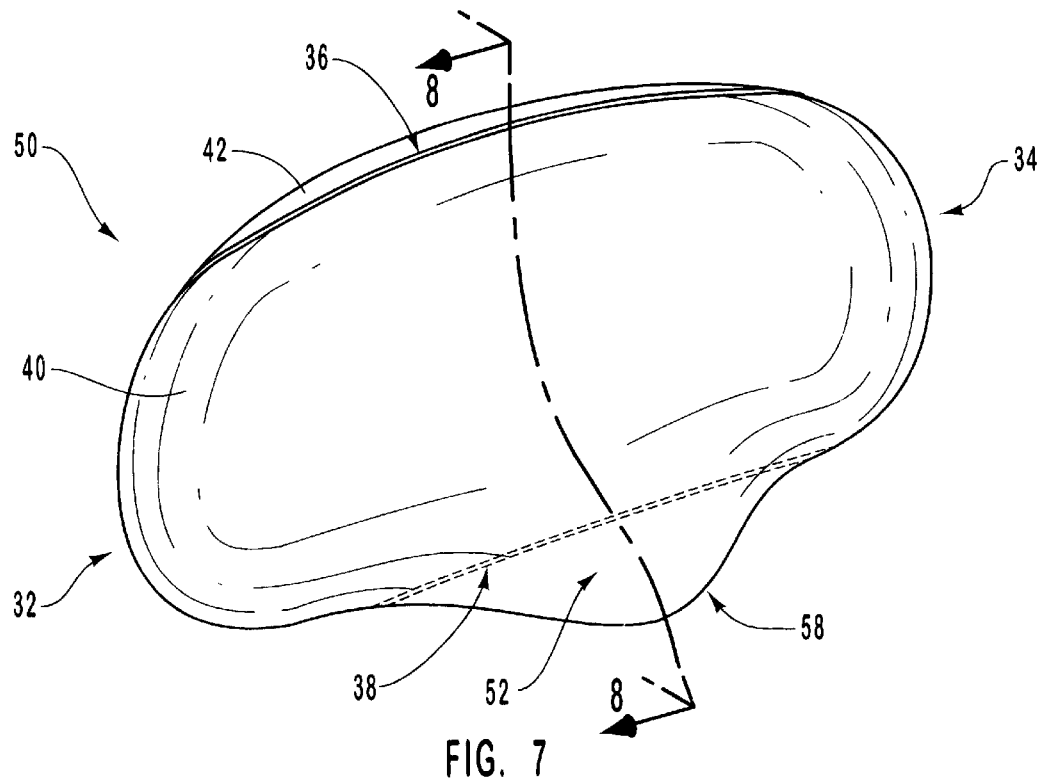
FIG. 7 is a top perspective view of an alternative embodiment of a matrix band of the invention that includes a flange extending away from the bottom edge of the matrix band.

In some circumstances the hollow formed in a tooth to be repaired is very deep. It may be desirable in these, as well as other suitable circumstances, for the matrix band to further include a flange or other extension for providing a form for the entire dental preparation. As shown in FIG. 7, the matrix band of the present invention can be configured with such a flange.

FIG. 7 illustrates a top perspective view of matrix band 50 which may advantageously be substantially identical to matrix band 30 of FIG. 2, except for the fact that matrix band 50 further comprises flange 52. During use, flange 52 biases against the lower proximities of the tooth for providing form for filling a hollow that is very deep. Flange 52 is also beneficial for providing support and stability to matrix band 30, even when the prepared hollow is not particularly deep.

Figure 8:
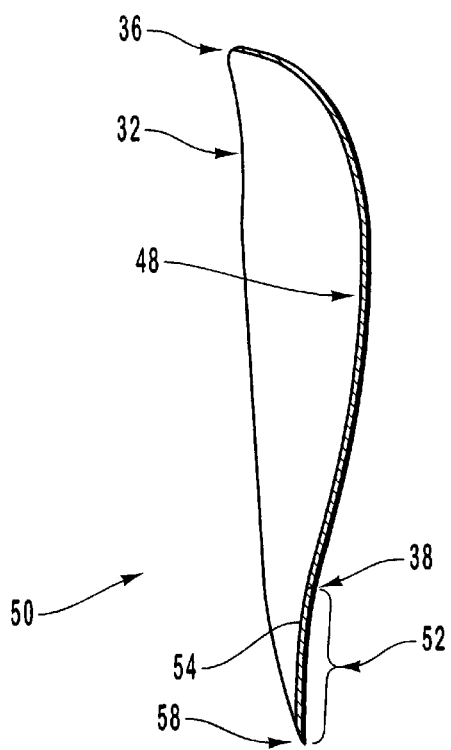
FIG. 8 is a cross-sectional view of the matrix band of FIG. 7 taken along line 8—8 illustrating the curvature of the flange in the latitudinal direction relative to the curvature of the remainder of the matrix band.

FIG. 8 is a cross-sectional view of matrix band 50 of FIG. 7 taken along line 8—8. As shown, matrix band 50 is substantially similar to matrix band 30 depicted in FIGS. 2–6, but further includes a convex flange curvature 54 that extends from what would otherwise be the bottom edge 38 to the lower flange edge 58. As in matrix band 30, matrix band 50 includes a first radius extending from top edge 36 downward to approximately one third of the total distance between top edge 36 and original bottom edge 38. The second radius extends over the remaining two thirds distance down toward original bottom edge 38 and has a magnitude that is approximately three times the magnitude of the first radius. According to the presently preferred embodiment, the magnitude of the first radius of matrix band 50 is approximately ⅛ inch and the magnitude of the second radius is approximately ⅜ inch.

In a preferred embodiment, flange curvature 54 is generally convex and is defined by a third radius. The third radius is an external radius that causes the flange 52 to curve away from bottom edge 38 in a direction opposite to the curvatures the first radius and the second radius. In one embodiment the third radius comprises a magnitude that is approximately ¼ inch, which is twice the magnitude of the first radius. Of course, it will be appreciated that the curvature of the flange 52 may have any desired orientation and radius of curvature.

Although the forgoing description goes into considerable detail regarding the various radii that define the asymmetrical latitudinal curve 48, it should be appreciated that the magnitudes and proportional relationships of the various radii can be altered to accommodate various sizes and contours of different types of teeth, as may occur from person to person or within a person's own set of teeth.

Matrix bands having various different curvatures and sizes can also be advantageously assembled into kits that can be provided to dental practitioners. A kit comprising multiple-sized and shaped matrix bands is useful because the sizes and shapes of teeth can vary from patient to patient. By providing a kit with multiple embodiments of the matrix band, a practitioner is able to selectively use the matrix band of the invention that is most appropriately configured in size and shape to provide a desirable contour for restoring a particular tooth.

The matrix bands of the invention, as have been described herein, include an asymmetrical shape for providing an appropriate form for molding dental fillings into a shape that more closely approximates the original shape of the tooth to be restored and for molding the resultant filling with a contact point that is located in an anatomically correct location. It should be appreciated that these benefits of the invention are advantages over the prior art.

It should also be appreciated that the present invention may be embodied in other forms without departing from its spirit or essential characteristics. As properly understood, the preceding description of specific embodiments is illustrative only and in no way restrictive. The scope of the invention is, therefore, indicated by the appended claims as follows.

What is claimed and desired to be secured by United States Letters Patent is:

1. An anatomically contoured matrix band for providing form when filling a tooth, comprising:
    a strip of flexible material that is sufficiently thin so as to fit between a tooth to be filled and an adjacent tooth;
    said strip comprising a length, generally defined by a first end and a second end of said strip, in a longitudinal direction sufficient to at least partially wrap around the tooth to be filled;
    said strip further comprising a height in a latitudinal direction sufficient for said strip to substantially enclose a hollow in a side of the tooth to be filled, said strip having an asymmetric latitudinal curvature while in an initial relaxed condition such that formation of a contact point of a dental restoration on a tooth occurs at an approximately correct anatomical location when said strip is wrapped at least partially around the tooth to be filled, said asymmetric latitudinal curvature spanning at least part of said length of said strip including a location approximately midway between said first and second ends of said strip.

2. An anatomically contoured matrix band as defined in claim 1, wherein said strip further has a longitudinal curvature while in an initial relaxed condition so as to facilitate wrapping of said strip at least partially around a tooth to be filled.

3. An anatomically contoured matrix band as defined in claim 2, wherein said longitudinal curvature is defined by a single radius of curvature.

4. An anatomically contoured matrix band as defined in claim 3, wherein the said radius of curvature of the said longitudinal curvature is approximately ⅝ inch.

5. An anatomically contoured matrix band as defined in claim 1, wherein said asymmetric latitudinal curvature includes an upper latitudinal curvature defined by a first radius of curvature and a lower latitudinal curvature defined by a second radius of curvature that is greater than said first radius so that when said strip is wrapped at least partially around the tooth to be filled it will curve more tightly around an upper portion of the tooth and less tightly around a lower portion of the tooth.

6. An anatomically contoured matrix band as defined in claim 5, wherein said second radius of curvature is approximately three times greater than said first radius.

7. An anatomically contoured matrix band as defined in claim 5, wherein said first radius of curvature is approximately ⅛ inch.

8. An anatomically contoured matrix band as defined in claim 5, wherein said second radius of curvature is approximately ⅜ inch.

9. An anatomically contoured matrix band as defined in claim 5, wherein said upper and lower latitudinal curvatures intersect approximately 1/3 of the way down from an upper edge of said strip toward a lower edge of said strip so as to facilitate formation of an anatomically correct contact point in the tooth to be filled.

10. An anatomically contoured matrix band as defined in claim 1, further including a flange extending from a lower edge of the said strip.

11. An anatomically contoured matrix band as defined in claim 1, wherein said strip has a cross-sectional thickness of approximately 0.0015 inch.

12. An anatomically contoured matrix band for providing form when filling a tooth, comprising:
  a strip of a flexible material that is sufficiently thin so as to fit between a tooth to be filled and an adjacent tooth;
  said strip comprising a length in a longitudinal direction, generally defined by a first end and a second end of said strip, sufficient to at least partially wrap around the tooth to be filled, said strip having a longitudinal curvature while in an initial relaxed condition so as to facilitate wrapping of said strip at least partially around the tooth to be filled;
  said strip further comprising a height in a latitudinal direction sufficient for the said strip to substantially enclose a hollow in a side of the tooth to be filled, said strip having an asymmetric latitudinal curvature while in an initial relaxed condition such that formation of a contact point of a dental restoration on a tooth occurs at an approximately correct anatomical location when said strip is wrapped at least partially around the tooth to be filled, said asymmetric latitudinal curvature spanning at least part of said length of said strip including a location approximately midway between said first and second ends of said strip, wherein said asymmetric latitudinal curvature is defined by a first radius of curvature provided at an upper portion of said strip and a second radius of curvature provided at a lower portion of said strip, said second radius being greater than said first radius so that when said strip is wrapped at least partially around the tooth to be filled it will curve more tightly around an upper portion of the tooth and less tightly around a lower portion of the tooth.

13. An anatomically contoured matrix band as defined in claim 12, wherein said second radius of curvature is approximately three times greater than said first radius.

14. An anatomically contoured matrix band as defined in claim 12, wherein said first radius of curvature is approximately 1/8 inch.

15. An anatomically contoured matrix band as defined in claim 12, wherein said second radius of curvature is approximately 3/8 inch.

16. An anatomically contoured matrix band as defined in claim 12, wherein said longitudinal curvature is defined by a single radius of curvature such that said longitudinal curvature is substantially symmetric.

17. An anatomically contoured matrix band as defined in claim 12, wherein said radius of curvature of said longitudinal curvature is approximately 5/8 inch.

18. An anatomically contoured matrix band as defined in claim 12, wherein said first and second radii of curvature intersect approximately 1/3 of the way down from an upper edge of said strip toward a lower edge of said strip so as to facilitate formation of an anatomically correct contact point in the tooth to be filled.

19. An anatomically contoured matrix band as defined in claim 12, wherein said strip has a cross-sectional thickness of approximately 0.0015 inch.

20. An anatomically contoured matrix band for providing form when filling a tooth, comprising:
  a strip of a flexible material that is sufficiently thin so as to fit between a tooth to be filled and an adjacent tooth;
  said strip comprising a length in a longitudinal direction, generally defined by a first end and a second end of said strip, sufficient to at least partially wrap around the tooth to be filled, said strip having a longitudinal curvature while in an initial relaxed condition so as to facilitate wrapping of said strip at least partially around the tooth to be filled;
  said strip further comprising a height in a latitudinal direction sufficient for said strip to substantially enclose a hollow in a side of the tooth to be filled, said strip in said latitudinal direction having an asymmetric latitudinal curvature while in an initial relaxed condition, said asymmetric latitudinal curvature spanning at least part of said length of said strip including a location approximately midway between said first and second ends of said strip, wherein said asymmetric latitudinal curvature is defined by a first radius of curvature provided for approximately an upper one third of said latitudinal curvature and a second radius of curvature provided for a remaining approximately lower two thirds of said latitudinal curvature, said second radius being greater than said first radius by a ratio of approximately 3 to 1 so that when said strip is wrapped at least partially around the tooth to be filled it will curve more tightly around an upper portion of the tooth and less tightly around a lower portion of the tooth so as to facilitate formation of a contact point of a tooth restoration at an approximately correct anatomical location; and
  said strip further including a flange extending from a lower edge of said strip and having a third radius of curvature that is different from said first and second radii of curvature.

21. An anatomically contoured matrix band for providing form when filling a tooth, comprising:
  a strip of flexible material that is sufficiently thin so as to fit between a tooth to be filled and an adjacent tooth;
  said strip comprising a length in a longitudinal direction sufficient to at least partially wrap around the tooth to be filled;
  said strip further comprising a height in a latitudinal direction sufficient for said strip to substantially enclose a hollow in a side of the tooth to be filled, said strip having an asymmetric latitudinal curvature spanning a majority of said length of said strip while in an initial relaxed condition such that formation of a contact point of a dental restoration on a tooth occurs at an approximately correct anatomical location when said strip is wrapped at least partially around the tooth to be filled.

* * * * *

UNITED STATES PATENT AND TRADEMARK OFFICE
CERTIFICATE OF CORRECTION

PATENT NO. : 6,712,608 B2  Page 1 of 1
DATED : March 30, 2004
INVENTOR(S) : Dan J. Bills It is certified that error appears in the above-identified patent and that said Letters Patent is hereby corrected as shown below:

Column 2,
Line 5, after "placed" change "to" to -- too --

Column 8,
Line 48, after "wherein" remove "the"

Signed and Sealed this

Third Day of May, 2005

JON W. DUDAS
*Director of the United States Patent and Trademark Office*